(12) United States Patent
Ungerstedt

(10) Patent No.: US 11,672,416 B2
(45) Date of Patent: Jun. 13, 2023

(54) DEVICE FOR USE IN THE TREATMENT OF HEMORRHOIDS

(71) Applicant: Developeration AB, Enskede (SE)

(72) Inventor: Johan Ungerstedt, Enskede (SE)

(73) Assignee: DEVELOPERATION AB, Enskede (SE)

( * ) Notice: Subject to any disclaimer, the term of this patent is extended or adjusted under 35 U.S.C. 154(b) by 539 days.

(21) Appl. No.: 16/755,442

(22) PCT Filed: Oct. 12, 2018

(86) PCT No.: PCT/SE2018/051044
§ 371 (c)(1),
(2) Date: Apr. 10, 2020

(87) PCT Pub. No.: WO2019/074439
PCT Pub. Date: Apr. 18, 2019

(65) Prior Publication Data
US 2020/0237205 A1      Jul. 30, 2020

(30) Foreign Application Priority Data
Oct. 13, 2017 (SE) .................................. 1751278-1

(51) Int. Cl.
*A61B 1/31* (2006.01)
*A61B 1/018* (2006.01)
(Continued)

(52) U.S. Cl.
CPC ................ *A61B 1/31* (2013.01); *A61B 1/018* (2013.01); *A61B 1/32* (2013.01); *A61B 17/0482* (2013.01);
(Continued)

(58) Field of Classification Search
CPC .................. A61B 1/31–317; A61B 2017/3452
See application file for complete search history.

(56) References Cited

U.S. PATENT DOCUMENTS 4,898,169 A * 2/1990 Norman ............. A61B 18/1485
606/45
7,695,432 B2    4/2010 Scheyer
(Continued)

FOREIGN PATENT DOCUMENTS

EP        2163211 A2    3/2010
WO    2006033122 A1    3/2006

OTHER PUBLICATIONS

International Search Report from corresponding International Application PCT/SE2018/051044 dated Dec. 6, 2018, 4 pages.

*Primary Examiner* — Matthew J Lawson
(74) *Attorney, Agent, or Firm* — Cooper Legal Group, LLC; Ronald M. Kachmarik

(57) ABSTRACT

A device for use in the treatment of hemorrhoids. The device includes an elongated tube-shaped element that includes a forward end and an aft end. The aft end provides access to the interior of the tube-shaped element. The tube-shaped element extends along a longitudinal axis L and includes at least one opening formed between the forward and aft end. The device includes an anal mucosa support device removably arranged within the tube shape element. The support device includes at least two cavities to receive anal mucosa. At least one needle guide structure is formed in the elongated tube-shaped element and the anal mucosa support device such that at least one needle is capable of being guided during movement within the tube-shaped element across the at least two cavities in the anal mucosa support device to a position where the needle extends across the opening in the tube-shaped element.

19 Claims, 14 Drawing Sheets

(51) Int. Cl.
  *A61B 1/32* (2006.01)
  *A61B 17/04* (2006.01)
  *A61B 17/00* (2006.01)
  *A61B 17/06* (2006.01)
  *A61B 17/30* (2006.01)

(52) U.S. Cl.
  CPC ............... *A61B 2017/00818* (2013.01); *A61B 2017/06042* (2013.01); *A61B 2017/306* (2013.01)

(56) References Cited

U.S. PATENT DOCUMENTS

| | | | |
|---|---|---|---|
| 8,337,401 B2* | 12/2012 | Rebuffat | A61B 1/31 600/184 |
| 8,475,362 B2* | 7/2013 | Sohn | A61B 17/3423 600/137 |
| 2005/0228371 A1* | 10/2005 | West | A61B 1/00087 606/41 |
| 2006/0167473 A1* | 7/2006 | Scheyer | A61B 1/00177 606/139 |
| 2006/0264706 A1* | 11/2006 | Piskun | A61B 17/320016 600/105 |
| 2010/0130857 A1* | 5/2010 | Szinicz | A61B 8/12 600/235 |
| 2011/0201895 A1* | 8/2011 | Bastia | A61B 1/31 600/219 |
| 2013/0110139 A1* | 5/2013 | Piskun | A61B 17/00234 606/153 |
| 2021/0030424 A1* | 2/2021 | Bhowmick | A61B 1/31 |

* cited by examiner

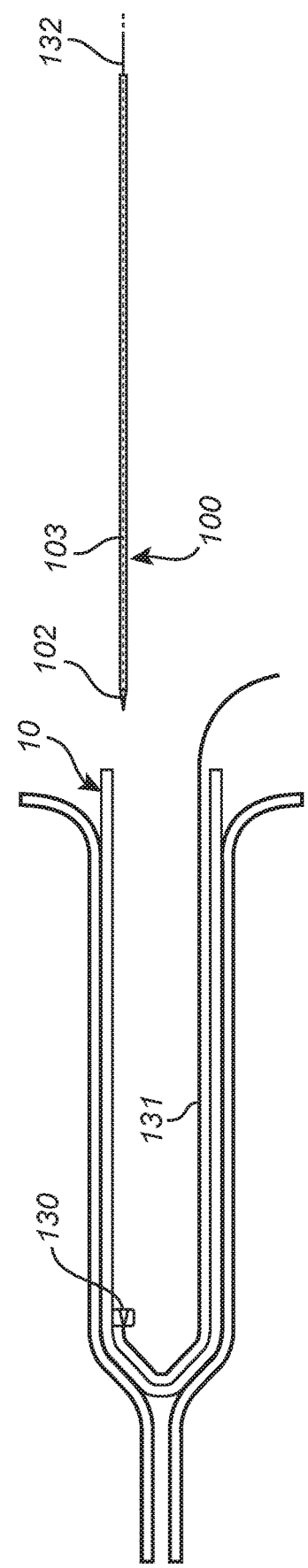

DEVICE FOR USE IN THE TREATMENT OF HEMORRHOIDS

TECHNICAL FIELD

The present invention relates to a device for use in the treatment of hemorrhoids.

TECHNICAL BACKGROUND

Up to 25% of the population older than 50 years are suffering from hemorrhoids. Hemorrhoids can be painful and cause severe problems for the affected persons.

There are several methods of treatment, all associated with varying degrees of complications. One of the most used modern techniques employs occlusion of blood-supplying arteries to the anus with a ligature; thereafter the mucosa is lifted through 4-5 stitches and secured in the lifted position.

One device intended to be used for the above described surgical treatment is disclosed in EP 1 683 47381. The elongated device is introduced in the rectum of the patient and makes it possible for the surgeon to ligate the arteries to the rectum by using a built-in ultrasonic device and access the anal mucosa via the space within the device and an opening formed in the surrounding wall of the device. To restore the anatomical position of the hemorrhoid the mucosa of the rectum needs to be lifted inwards by several stiches placed by the surgeon (mucopexy). By turning the device the mucosa is gradually accessible for further suturing. A total of 6-8 sutures are placed. After the suturing, a knot is placed to lift the rectum mucosa inwards and the hemorrhoid is repositioned to its anatomically normal position and the symptoms are reduced.

The disclosed device facilitates the surgeon's sewing but the stiches are placed by hand which is time consuming. Furthermore, sewing by hand results in variations in suture depth and length which will have an impact on the final result of the treatment. The disclosed device requires general anesthesia due to the space required when the stiches are placed by hand, which limits the treatment to patients who are able to receive general anesthesia and increases the treatment cost considerably.

An alternative device for treatment of hemorrhoids is disclosed in EP2163211. The disclosed device is intended for surgical stapling to generate the desired treatment of hemorrhoids by cutting away and stapling the mucosa together again and thereby lifting the mucosa by 2-3 cm. The treatment is effective but is associated with severe complications including postoperative pain, sepsis and even death. The cost is high due to the necessity of anesthesia and the cost of the device.

There is consequently a need for an improved device for treatment of hemorrhoids that reduces the surgery time and treatment cost and improves the outcome of the surgery without the need of ligating the artery to the rectum.

SUMMARY OF THE INVENTION

The present invention relates to a device for use in the treatment of hemorrhoids that addresses the problems defined above, for example, with improved handling, faster surgical intervention and a lower treatment cost.

The device for use in the treatment of hemorrhoids comprises:

an elongated tube-shaped element comprising a forward end and an aft end, said aft end being open such that the interior of the tube-shaped element is accessible via the aft end, said tube-shaped element extending along a longitudinal axis L and comprising at least one opening formed between the forward and aft end; and an anal mucosa support device removably arranged within the tube shape element at the opening and comprising a least two cavities for the anal mucosa arranged along the longitudinal axis L, wherein at least one needle guide structure is formed in the elongated tube-shaped element and the anal mucosa support device such that at least one needle is guided during movement within the tube-shaped element from an extracted position in which the needle is arranged outside the opening in the elongated tube-shaped element across the at least two cavities in the anal mucosa support device to a position where the needle extends across the opening in the tube-shaped element.

The device according to the invention is introduced in the rectum of the patient in order to make it possible for a surgeon to treat the hemorrhoids. Once the device is in the intended position, the prolapsed anal mucosa is arranged in the a least two cavities in the anal mucosa support device to ensure that the anal mucosa is in the correct starting position relative the device.

The needle guide structure, formed in the elongated tube-shaped element and the anal mucosa support device, provides a reliable and efficient guide for a needle during movement within the tube-shaped element from the extracted starting position across the at least two cavities in the hemorrhoid support device, i.e. through the anal mucosa arranged within the at least two cavities, to the position where the needle extends across the entire opening in the tube-shaped element.

The needle is used to introduce a suture thread, a staple or other such securing means through the anal mucosa. Different alternatives to enter the suture thread, the staple or other such securing means are described in the detailed description but generally this is achieved by introducing the suture thread, a staple or other such securing means together with the needle when the needle is moved from the retracted position to the extracted position, and then remove the needle such that the suture thread, the staple or other such securing means is remaining in the intended position through the anal mucosa. Alternatively the needle is first moved from the retracted position to the extracted position where the needle tip is secured in a coupling element of the suture thread, the staple or other such securing means such that the suture thread, the staple or other such securing means are introduced in the anal mucosa when the needle is retracted from the folds formed in the anal mucosa. As soon as the suture thread, staple or other such securing means is correctly positioned extending through the anal mucosa, the anal mucosa support device is removed from the opening and the device to free the anal mucosa and the suture thread, staple or other such securing means from the device which is essential to make it possible to tighten the suture thread, staple or other such securing means and permanently secure the suture thread, staple or other such securing means in the intended lifted position and, after the surgery is completed, remove the device from the rectum of the patient.

The device according to the invention facilitates the surgical treatment considerably since the needle guide structure and the anal mucosa support device ensures that the needle, and in the end the suture thread, staple or other securing means, is extending along the intended path through the intended area of the anal mucosa arranged in each of the cavities which ensures that the desired result is achieved. The guided needle path ensures that all surgical treatments will be conducted in the intended and correct way since the manual sewing is eliminated.

In the case of severe hemorrhoid problems, the rectum mucosa needs to be lifted more. The device may be improved further by increasing the number of cavities in the anal mucosa support device. For example, the anal mucosa could comprise five cavities arranged along the longitudinal axis L such that further folds on the anal mucosa are created and the lifting effect is increased considerably.

Furthermore, several studies have shown that results as good as those obtained by conventional methods can be achieved by lifting the rectum mucosa without ligating the artery supplying blood to the rectum.

Different types of suture wires, stamps or securing arrangements may be used with the device according to the invention. When the needle and suture thread, staple or other such securing means has been extended through the anal mucosa, the needle is removed and the suture thread, staple or other such securing means is tightened and permanently secured such that the desired lift of the prolapsed anal mucosa is achieved.

The disclosed device facilitates the surgeon's treatment of hemorrhoids by mucopexy with less variations in the operation procedure, suture depth and distance, since the needle is guided along the intended path through the anal mucosa. The device also ensures faster surgical intervention and makes it possible to conduct the surgical treatment without the need of general anesthesia due to the smaller diameter of the device, which in turn results in considerably lower treatment cost.

The claimed device for use in the treatment of hemorrhoids may comprise more than one opening in the tube-shaped element and corresponding anal mucosa support devices and needle guide structures arranged around the periphery of the elongated tube-shaped element to make it possible to perform surgical treatment in two or more regions within the rectum of the patient without changing the position of the device. The fact that treatment may be provided in more than one area may reduce the overall time for the surgical treatment.

In one embodiment of the device, the at least one needle is moved from the extracted position to the position where the at least one needle extends across the opening in the tube-shaped element substantially parallel to the longitudinal axis L. This embodiment is favourable since it is easy for the surgeon to control and move the at least one needle via the open end of the elongated tube-shaped element when the needle is guided substantially parallel to axis L.

In one embodiment of the device, the at least one needle guide structure comprises at least one needle passage arranged in the opening in the elongated tube-shaped element to guide the at least one needle during movement from the extracted position to the position where the needle extends across the opening in the tube-shaped element. This embodiment ensures that the needle is extending in the intended direction across the opening. Further needle passages along the intended direction of the needle provide further guidance during insertion of the needle.

In one embodiment of the device, the at least one needle guide structure comprises needle guide elements arranged in the elongated tube-shaped element on each side of the opening in the tube-shaped element to guide the needle. This embodiment is favourable since the needle is guided on both sides of the opening.

In one embodiment of the device, the at least one needle passage is formed in the contact surface between the elongated tube-shaped element and the anal mucosa support device such that the at least one needle passage is opened when the anal mucosa support device is removed from the elongated tube-shaped element. This embodiment is favourable since the needle and/or the suture wire, stamp or other such securing arrangement is easily released from the device which is necessary to extract the device from the rectum of the patient.

In one embodiment of the device, the anal mucosa support device comprises a first and a second elongated part extending substantially parallel to axis L, said first and second part are arranged adjacent to each other and the at least one needle passage formed in the contact surface between the first and second part such that the at least one needle passage is opened when the first and second part are separated from each other. This embodiment is favourable since the needle and/or the suture wire, stamp or other such securing arrangement is released in an effective way from the device.

One embodiment of the device comprises two needle guide structures formed in the elongated tube-shaped element and the anal mucosa support device such that two needles are guided during movement within the tube-shaped element from an extracted position in which the needles are arranged outside the opening in the elongated tube-shaped element across the at least two cavities in the anal mucosa support device to a position where the needles extend across the opening in the tube-shaped element. This embodiment is favourable since this embodiment provides for two suture wires, stamps or other such securing arrangements side by side which reduces the risk for failure, tearing of the tissue/mucosa or reduced effect of the intended lift of the anal mucosa and provides a stronger, more resistant lifting effect.

In one embodiment of the device, the anal mucosa support device comprises a first, a second and an intermediate elongated part extending substantially parallel to axis L, said first and second part are arranged on opposite sides of the intermediate part adjacent to the intermediate part such that one needle passage is formed in the contact surface between the first part and the intermediate part, and second needle passage is formed in the contact surface between the intermediate part and the second elongated part such that the two needle passages are opened when the first, second and intermediate elongated part are separated from each other. This embodiment of the anal mucosa support device provides an efficient guide for both needles during movement from the retracted position across the opening in the tube-shaped element.

In one embodiment of the device, the two needle guide structures are arranged to guide the two needles substantially parallel from the extracted position in which the needles are arranged outside the opening in the elongated tube-shaped element across the at least two cavities in the anal mucosa support device to the position where the needles extend across the opening in the tube-shaped element. The two needles are furthermore guided in a direction substantially parallel to the longitudinal axis which is favourable since it facilitates the surgeon's ability to insert and move the needles via the open end of the tube-shaped element.

In one embodiment of the device, the tube-shaped element is divided into at least a forward and a rear part and said forward part is removably attached to the rear part in order to facilitate the manufacturing of the tube-shaped element and the assembly of the different components arranged within the tube-shaped element.

In one embodiment of the device, a sealing plug is arranged to close and seal the open aft end of the device. A connection with access to the interior of the tube-shaped element is attached to pumping means to reduce the pressure within the tube-shaped element and suck the anal mucosa into the at least two cavities to facilitate the treatment of the patient. The pumping means is for example a manual or electrically powered pump or an externally arranged source of sucking action, such that the anal mucosa may be sucked into the at least two cavities of the device.

In one embodiment of the device, the sealing plug comprises the connection to the pumping means.

In one embodiment of the device, the device comprises a handle extending in substantially radial direction from the longitudinal axis L from the aft end of the tube-shaped element and the connection with access to the interior of the tube-shaped element is arranged in the handle.

In one embodiment of the device, the at least two cavities in the anal mucosa support device comprises a bottom structure and the distance in radial direction from axis L between the centre of the needle passage and the bottom structure is between 2 and 12 mm. This embodiment provides a reliable securing once the suture thread, staples or other such securing means is tensioned and permanently secured since the fold of the anal mucosa will have sufficient strength and not break.

In one embodiment of the device, the bottom structure comprises at least one opening in each cavity such that the anal mucosa is sucked into the at least two cavities. This embodiment is favourable since the anal mucosa will be sucked towards the bottom structure ensuring the same suture depth in the anal mucosa at every procedure.

In one embodiment of the device, the at least two cavities in the anal mucosa support device comprise a bottom structure, and the cavity arranged in the forward end of the anal mucosa support device along axis L is longer than that of the at least one other cavity. This embodiment provides a reliable securing once the suture thread, staple or securing means is tensioned and permanently secured since the fold in the inner end of the treated area will be larger than the other fold, or folds, and thereby provide a reliable securing of the anal mucosa folds and ensure the desired inward lift of the anal mucosa.

In one embodiment of the device, the anal mucosa support device is maintained in the intended position within the tube-shaped element by a locking element removably arranged within the tube-shaped element to force the anal mucosa support device into the intended position with the at least two cavities exposed in the opening of the tube-shaped element. This embodiment is favourable since the anal mucosa support device, when the locking element is removed, could be moved radially inwards and easily removed from the opening in the tube shape element.

In one embodiment of the device, the locking element is forming a bottom surface in the cavities in the anal mucosa support device. This embodiment provides a device with less complicated structure and ensures that the device will work as intended.

One embodiment of the device comprising at least one closing element removably arranged in the tube-shaped element to close the at least one opening in the tube-shaped element and facilitate insertion of the device.

In one embodiment of the device, the closing element has a shape corresponding to the shape of the tube-shaped element to provide a smooth outer surface of the device and facilitate insertion of the device.

BRIEF DESCRIPTION OF THE DRAWINGS

The above as well as further objectives, features and advantages with the present invention will become apparent when studying the following illustrative and non-limiting detailed disclosure of preferred embodiments of the present invention, with reference to the appended drawings:

FIG. 11 illustrates schematically a third embodiment of use of suture thread for lifting the anal mucosa.

Figure 1:
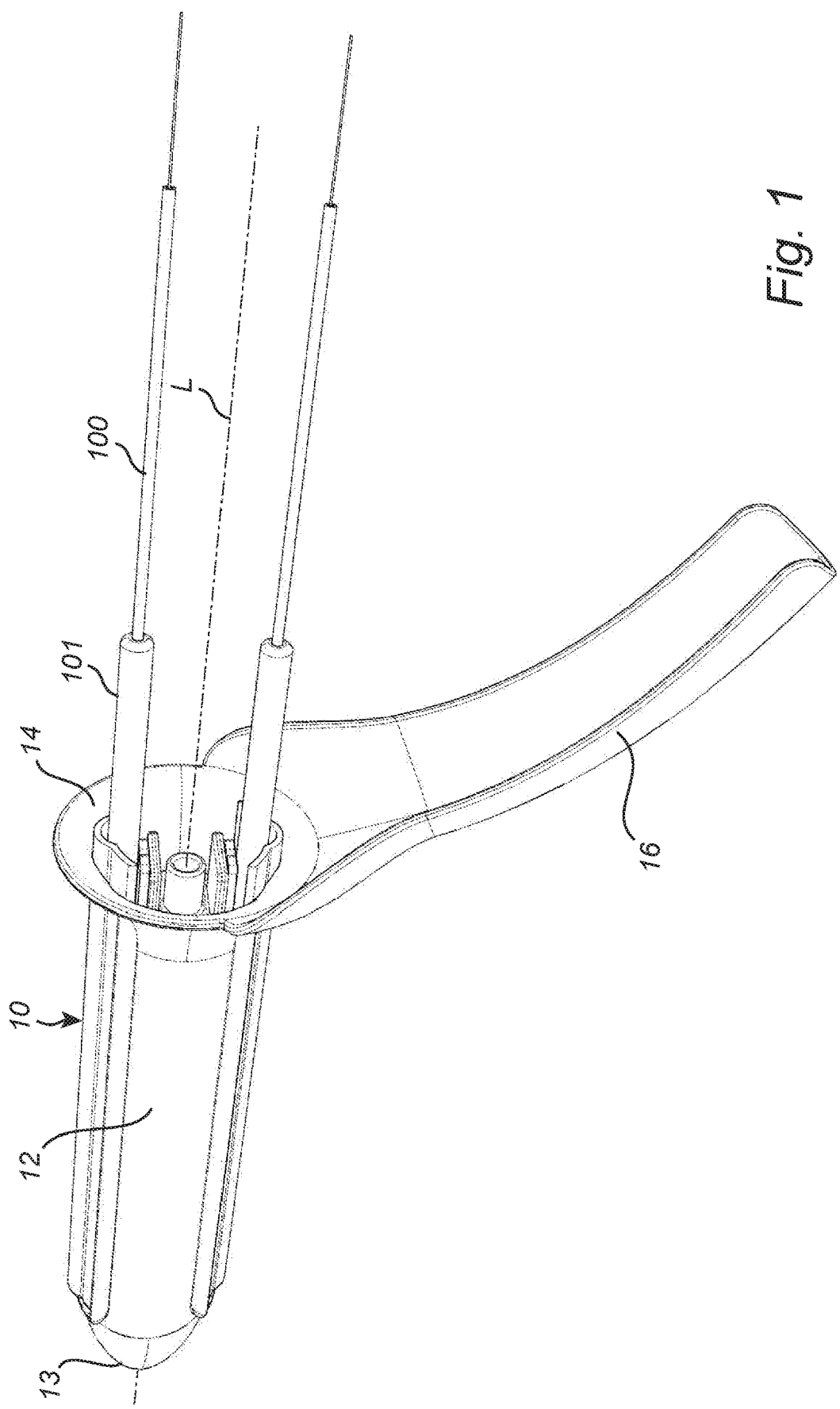
FIG. 1 illustrates a perspective view of the device according to the invention.

All figures are schematic, not necessarily to scale, and generally only illustrating selected parts which are necessary in order to elucidate the invention, wherein other parts may be omitted or merely suggested.

DETAILED DESCRIPTION

The present invention, as previously stated, relates to a device 10 for use in treatment of hemorrhoids. The device comprises an elongated tube-shaped element 12 that constitutes the outer casing of the device. The tube-shaped element 12 comprising a rounded forward end 13 that is intended to be arranged in the rectum of the patient. The tube-shaped element further comprises an open aft 14 end intended to be arranged outside the rectum of the patient during use of the device. The aft end 14 is slightly curved outwards. Within the tube-shaped element an interior cavity accessible via the open aft end 14 is formed. The tube-shaped element is substantially straight and extending along a longitudinal axis L. The tube-shaped element could be made in different lengths and the cross-sectional shape of the tube-shaped element transverse to axis L is substantially circular in order to facilitate the insertion of the device when the treatment is initiated. Alternative cross-sectional shapes could also be oval, triangular, rectangular, pentagonal or hexagonal, etc. with rounded corners. The tube-shaped element is preferably made of a plastic material.

Figure 2:
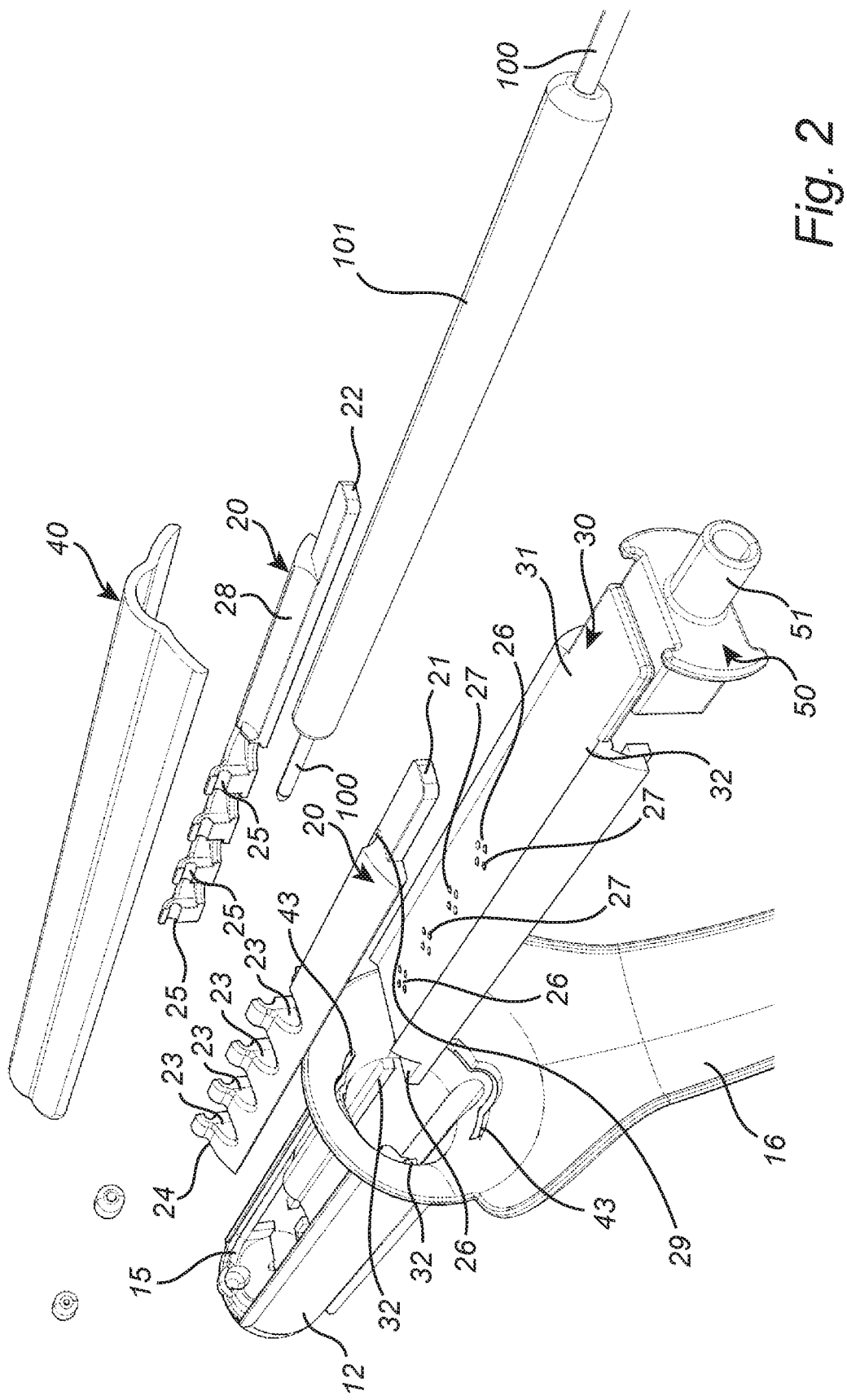
FIG. 2 illustrates an exploded view of the device in FIG. 1.

The tube-shaped element furthermore comprises at least one opening 15, illustrated in FIG. 2, formed in the tube-shaped element wall and arranged between the forward 13 and aft end 14. The opening 15 has substantially the same width transverse to the axis L and extend between the forward and aft end. Furthermore a handle 16 is extending in substantially radial direction from axis L from the aft end of the tube-shaped element to facilitate movement of the device during use. Further handles could be provided and the design of the handle modified in different ways within the scope of the invention.

The device 10 furthermore comprises an anal mucosa support device 20, illustrated for example in FIG. 2. The illustrated embodiment of the anal mucosa support device comprises a first 21 and a second 22 elongated part arranged to extend substantially parallel to axis L. The first and second elongated part are arranged adjacent to each other and intended to be removably arranged within the tube shape element such that the anal mucosa support device 20, when arranged in the intended position within the tube-shaped element, is exposed in the opening 15 in the tube-shaped element 12. The anal mucosa support device comprises a least two cavities 23 for the anal mucosa but the illustrated embodiment comprises four cavities 23 with substantially equal size and a larger fifth cavity 24 formed by the forward end of the anal mucosa support device when arranged in the intended position in the tube-shaped element 12. The cavities 23, 24 are arranged along the longitudinal axis L substantially in the centre of the opening in the tube-shaped element. Each cavity has an open side facing the opening 15 in the tube-shaped element 12 such that the anal mucosa can enter each of the cavities.

The first 21 and a second 22 elongated part are designed to be arranged adjacent to each other substantially in the centre of the opening and each of the cavities 23, 24 are arranged along the contact surface between the first 21 and a second 22 elongated part such that the cavities are formed by substantially identical half cavities in the first and the adjacent second elongated part, i.e. half of the cavity is formed by one of the elongated parts and the other half of the cavity by the other elongated part. Furthermore, needle passages 25 are formed along the contact surface between the first and second part. The illustrated embodiment of the device comprises four needle passages 25, i.e. one needle passage between each of the cavities in the anal mucosa support device. The needle passages 25 are opened when the first and second part are separated from each other to release a needle, or a suture thread, a staple or other such securing means extending through the needle passage 25.

The needle passages 25 constitutes the needle guide structure formed in the elongated tube-shaped element 12 and the anal mucosa support device 20 such that a needle 100 is guided during movement within the tube shaped element from an extracted position in which the needle is arranged outside the opening 15 in the elongated tube-shaped element 12 through the cavities in the anal mucosa support device to a position where the needle extends across the opening in the tube-shaped element. Each needle passage 25 has a size and shape corresponding to the cross-sectional dimension and shape of the needle such that the needle is able to easily pass through each needle passage when the needle is moved from the retracted to the extracted position. Preferably the side of the needle passage that is facing the aft end of the device is slightly widened to guide the needle into the centre of the needle passage 25.

Each cavity 23, 24 in the anal mucosa support device 20 comprises a bottom structure 26 and the distance in radial direction from axis L between the centre of the needle passage and the bottom structure is between 2 and 12 mm. In order to ensure that the anal mucosa is correctly arranged in the cavities 23, 24 in the anal mucosa support device 20, the bottom structure of each cavity comprises at least one opening 27 in each cavity, said openings 27 are connected to some sort of means that is able to provide a pressure below the surrounding pressure, such as for example a manually or electrically powered pump or an externally arranged source of sucking action, such that the anal mucosa is sucked into the cavities.

The anal mucosa support device 20 is removably arranged within the tube-shaped element 12 and maintained in the intended position within the tube-shaped element by a removable locking element 30. The locking element is shaped like an elongated plate 31 with a length, along axis L, and width corresponding to the interior dimensions of the elongated tube element.

The positioning and securing of the locking element within the tube-shaped element is provided by guiding rails 32 arranged along the inner peripheral wall of the tube-shaped element on each side of the opening in the tube-shaped element such that the locking element could slide parallel to the longitudinal axis L. The first and second element of the anal mucosa support is fitted within a recess 37 on the side of the locking element that is facing the opening 15 in the tube-shaped element such that the first and second element 21, 22 are maintained in the intended position. The locking element 30 is arranged within the tube-shaped element to force the anal mucosa support device 20 into the intended position and maintain the anal mucosa support device in the intended position with the cavities exposed in the opening of the tube-shaped element. In the illustrated embodiment of the anal mucosa support device and the locking element the cavities have an open bottom structure that is closed by the locking element 30.

Figure 3:
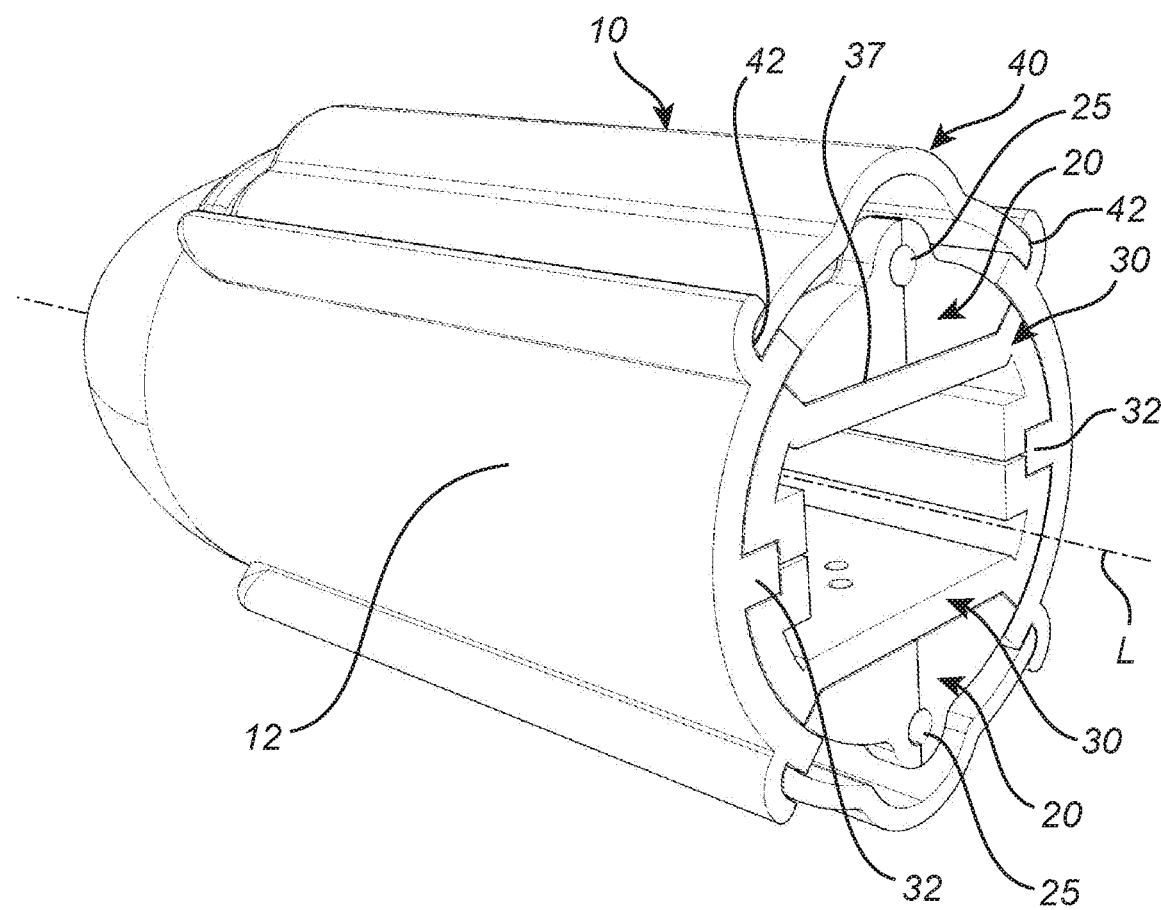
FIG. 3 illustrates a cross sectional view transverse to the longitudinal axis L of the device.

In the above description of the device 10 only one arrangement comprising one opening 15 in the tube-shaped element 12, one anal mucosa support device 20 and one locking element 30 has been described but preferably the device 10 is designed to comprise two, alternatively three or up to six similar, corresponding substantially identical arrangements each comprising one opening in the tube-shaped element, one anal mucosa support device and one locking element. If the device comprises two arrangements which are illustrated in FIG. 3, the openings are arranged opposite to each other in the tube-shaped element and if the device comprises three or more arrangements, these are arranged at substantially equal distance from each other around the tube-shaped element.

The device 10 is introduced in the rectum of the patient in order to make it possible for a surgeon to treat the hemorrhoids by surgery. Once the device is in the intended position, the prolapsed anal mucosa is arranged in the cavities 23, 24 in the anal mucosa support device 20. The needle guide structure, formed in the elongated tube-shaped element and the anal mucosa support device, provides guidance for the needle, or needles, 100 during movement within the tube-shaped element from the extracted starting position, through the cavities 23, 24, i.e. through the anal mucosa arranged within the cavities, to the position where the needle 100 extend across the entire opening 15 in the tube-shaped element 12 and through the anal mucosa arranged in the different cavities such that folds are generated in the anal mucosa.

The needle 100 is used to introduce a suture thread, a staple or other securing means through the different folds of the anal mucosa. Different alternatives to enter the suture thread, the staple or other such securing means could be used as understood by persons of ordinary skill in the art. Either the suture thread, staple or other such securing means is introduced together with the needle, or the needle is first moved from the retracted position to the extracted position where the needle tip is secured in a corresponding docking element 122 in the end of a suture thread, a staple or other such securing means arranged within the forward end of the device, illustrated in FIG. 10 and described in detail later in this description. The suture thread, the staple or other such securing means is introduced in the anal mucosa when the needle is retracted from the extracted position and the suture thread, the staple or other such securing means are drawn through the anal mucosa. As soon as the suture thread, staple or other such securing means is correctly positioned, the anal mucosa support device 20 removed from the opening and the device 10 via the open aft end 14 to free the anal mucosa and the suture thread, staple or other such securing means from the device which is essential to make it possible to remove the device from the rectum after the suture thread, staple or other such securing means are tightened and permanently secured.

The device 10 according to the invention facilitates the surgical treatment since the needle guide structure and the anal mucosa support device 20 ensures that the needle 100, and in the end the suture thread, staple or other such securing means, is extending through the intended area of the anal mucosa arranged in each of the cavities 23, 24 which ensures that the desired result is achieved.

In the case of severe hemorrhoid problems, the rectum mucosa needs to be lifted more. The device may be improved further by increasing the number of cavities in the anal mucosa support device such that further folds on the anal mucosa are created, which increases the lifting effect considerably.

The device 10 furthermore comprises one closing element 40 for each opening 15 in the tube-shaped element 12. The closing element 40 has a shape corresponding to the cross-sectional shape of the tube-shaped element 12 to provide a smooth outside shape of the device 10 and a length corresponding to the length of the opening 15 to completely close the opening when arranged in the device. The closing element is removably arranged in the tube-shaped element and intended to close the opening in the tube-shaped element to facilitate insertion of the device in the rectum of the patient. When the device is in the desired position in the rectum, the closing element that is extending all the way to the aft end of the device is removed via the aft end 14 of the tube-shaped element 12 to expose the opening in the tube-shaped element and make it possible for the anal mucosa to access the cavities. The closing element 40 is arranged to slide in substantially straight recesses 42, illustrated in FIG. 3, formed along the elongated sides of the opening 15 in the tube-shaped element substantially parallel to the longitudinal axis L. In the illustrated embodiment of the tube-shaped element and closing element, the closing element exits the tube-shaped element via a slot 43 in the curved section in the aft end 14 of the tube-shaped element 12. The slot has a shape corresponding to the shape of the closing element.

When the device is fitted in the intended position in the rectum of the patient and the closing element is removed, the open aft end 14 of the tube-shaped element 12 is closed by a sealing plug 50. The locking element 30 and the anal mucosa support 20 ends in the open aft end 14 of the tube-shaped element 12 and the sealing plug 50 is designed to fit in the open aft end 14 and close and seal the open aft end 14 of the device 10 such that pumping or suction means could be connected to the interior of the tube-shaped element 12 via a connection 51 in said sealing plug 50. The sealing plug could also be provided with an elastic tube extending from the plug to facilitate the connection to the pumping or suction means. Alternative embodiments to provide the desired connection of pumping or suction means to the interior of the tube-shaped elements are also possible. For example, the pumping or suction means could be connected to the interior of the device via a connection, not illustrated, arranged on the aft end of the device or the handle and a channel integrated in the device and connected to the interior of the tube-shaped elements 12. When the pumping or suction means, not illustrated, is activated the pressure within the tube-shaped element 12 is reduced and the anal mucosa is sucked into the cavities.

Once the anal mucosa is in the desired position within the cavities 23, 24, the needle 100 is pushed from the retracted position through the needle passages 25, across the cavities 13, 14 and the anal mucosa arranged in the cavities all the way to the opposite side of the opening 15 in the tube-shaped element 12.

The needle 100 is extending substantially parallel to the longitudinal axis L through a needle sleeve 101, illustrated in FIG. 2. The needle sleeve 101 is intended to be arranged within a space formed by a first sleeve support 28 in one of the elongated parts 22 and a corresponding adjacent second sleeve support 29 in the other elongated part 21 aft of the opening 15 in the tube-shaped element 12. The sleeve 101 is intended to maintain and support the needle 100 in the intended position within the tube-shaped element of the device 10 and guide the needle 100 during movement from the retracted position across the opening 15. The sleeve 101 is designed to provide a tight fitting to the exterior of the needle, and the first and second sleeve supports 28, 29 are designed to provide a tight fitting to the needle sleeve to prevent that air is leaking through the gaps between the needle and the needle sleeve as well between the needle sleeve and the first and second sleeve support 28, 29 from the surrounding space into the closed space within the tube-shaped element.

The needle is allowed to move forward and backwards in the sleeve 101. When the locking element 30 and the anal mucosa support device 12 is removed from the tube-shaped element, the needle sleeve 101 is released and either removed or used to facilitate the tensioning of the suture thread, staple or other fastening means to secure the anal mucosa in the lifted position.

Figure 4A:
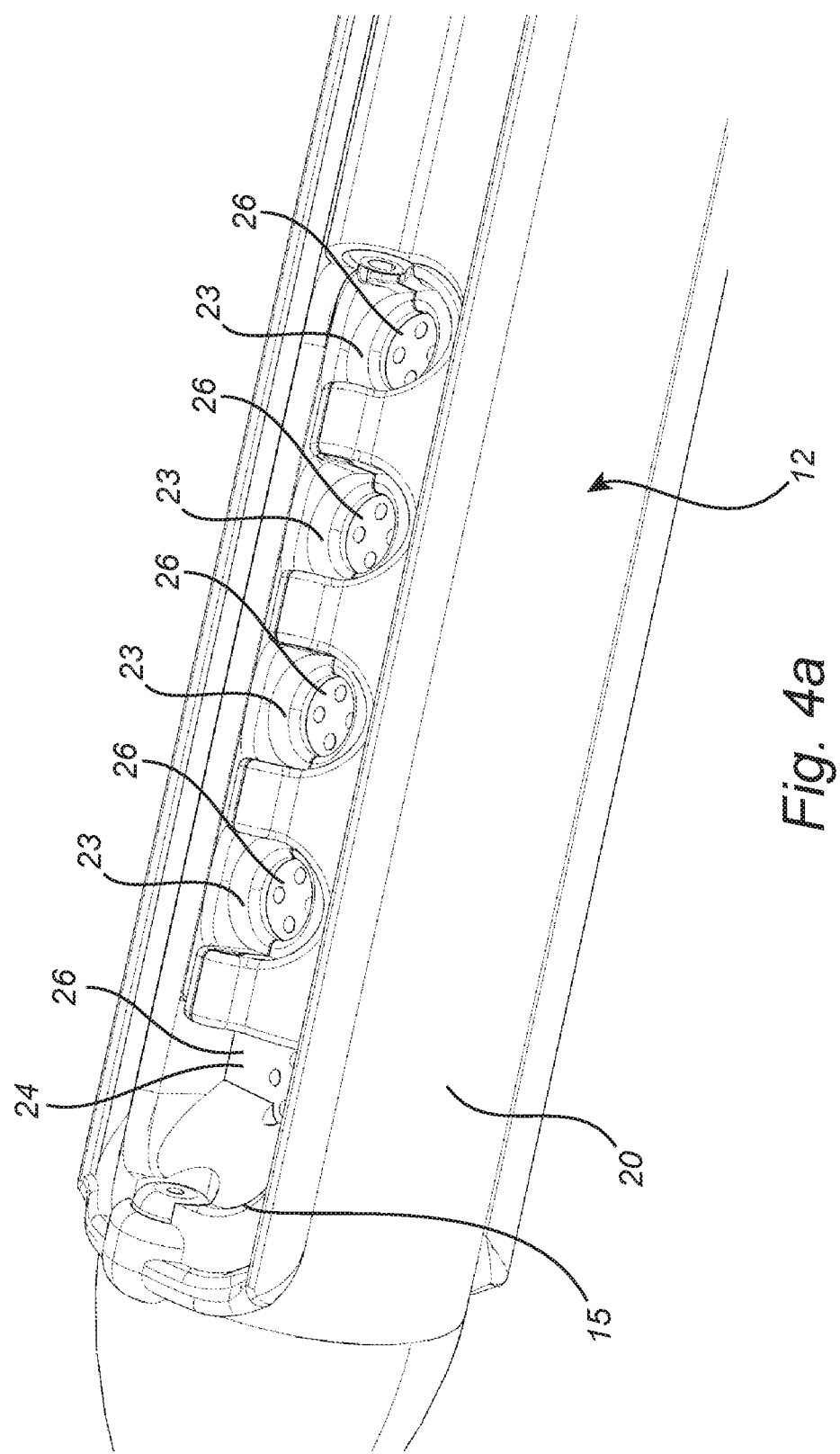
FIG. 4a illustrates selected parts of the device in FIG. 1 before the needle is inserted.

In FIG. 4a a perspective view of the device 10, the opening 15 in the tube-shaped element and the anal mucosa support device prior to the movement of the needle is illustrated. The device comprises four equally sized cavities 23 and one larger cavity 24 arranged in the forward end of the anal mucosa support device and the opening in the tube-shaped element. Each of the cavities comprises a bottom structure 26, and the bottom structure of the forward-most cavity 24 may be deeper than in the other cavities (i.e., more distant from the center of the needle passage) to generate a stronger and more resistant securing in the larger inner fold of the anal mucosa.

Figure 4B:
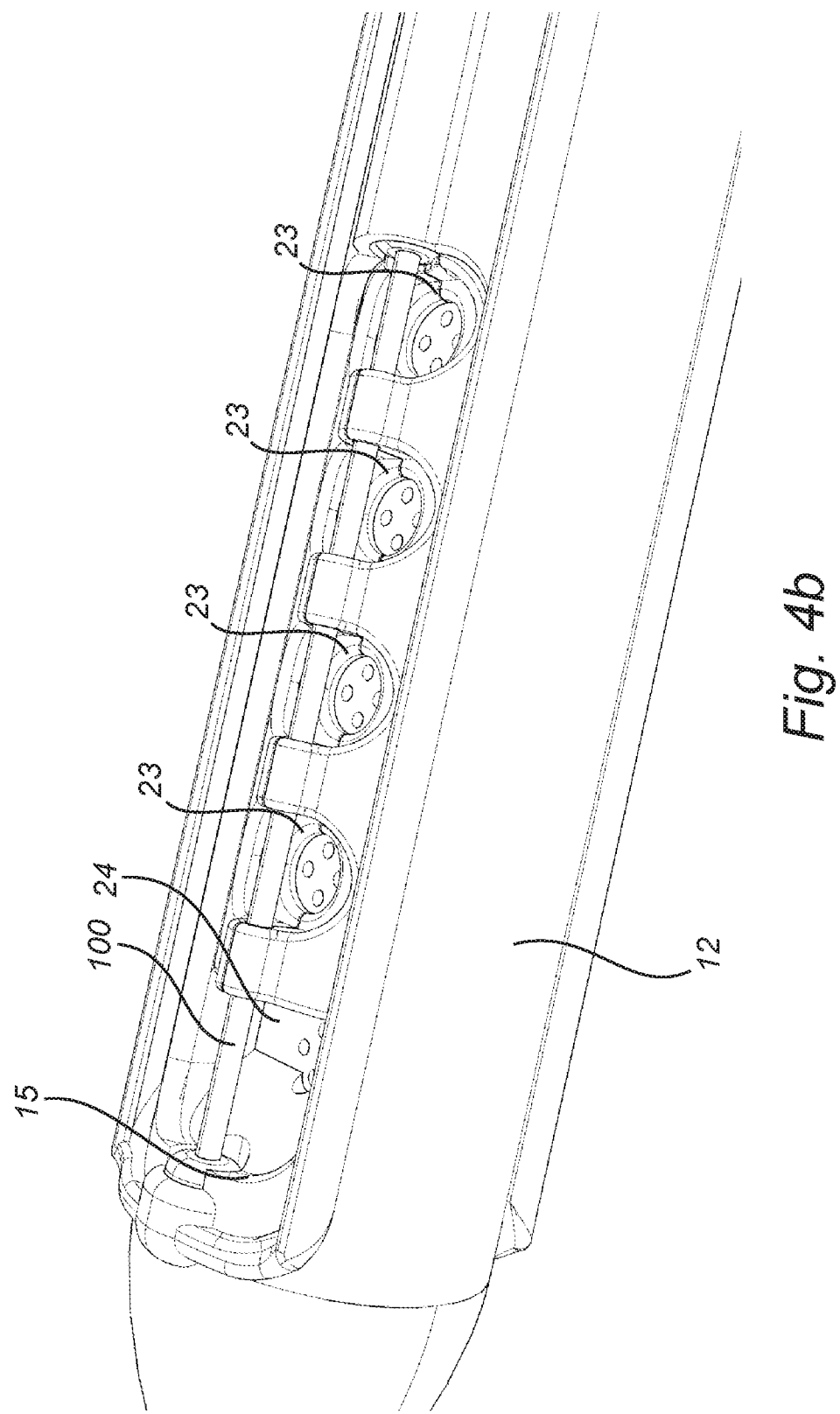
FIG. 4b illustrates selected parts of the device after the needle is inserted.
Figure 4C:
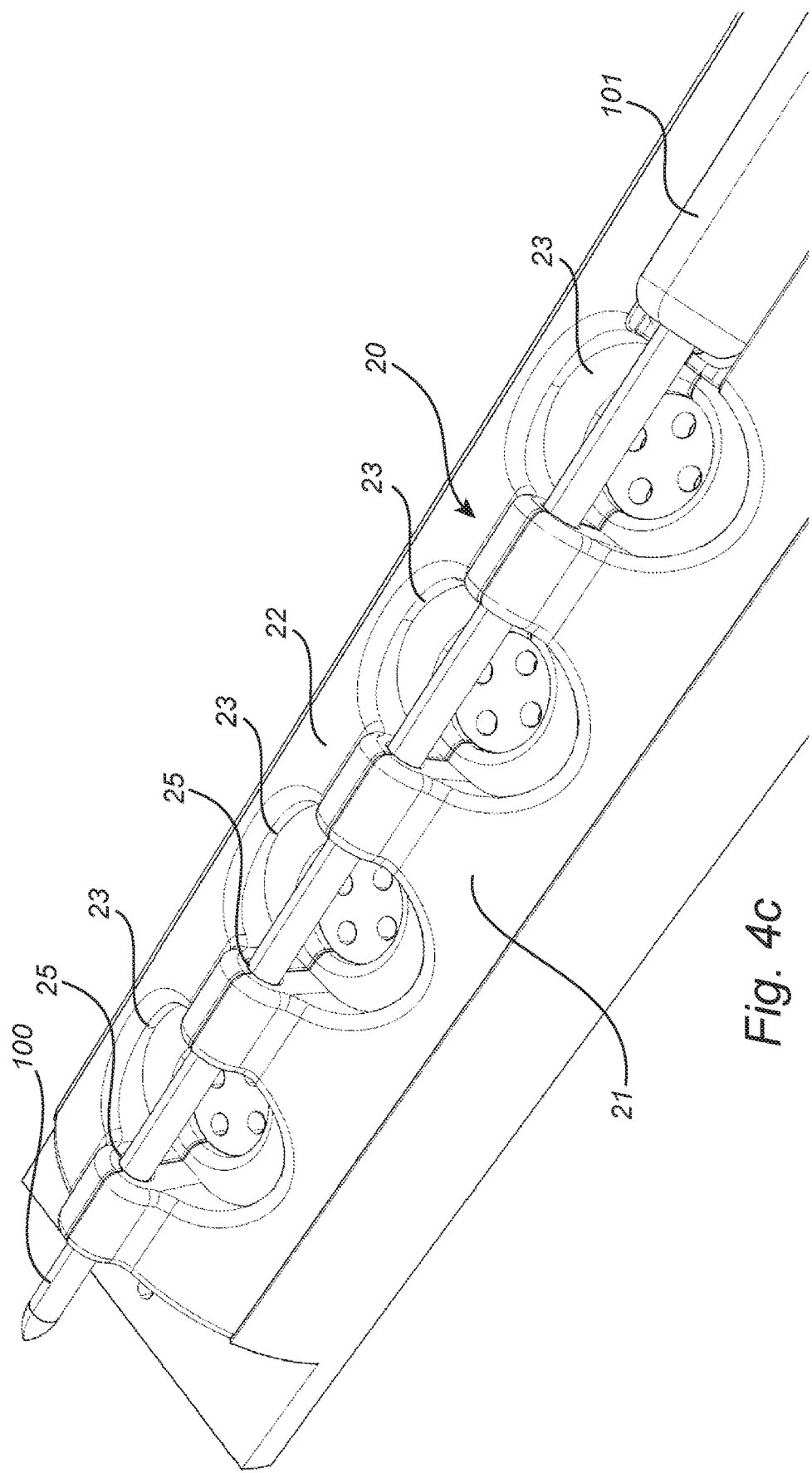
FIG. 4c illustrates selected parts of the device in FIG. 1 with the needle inserted.
Figure 4D:
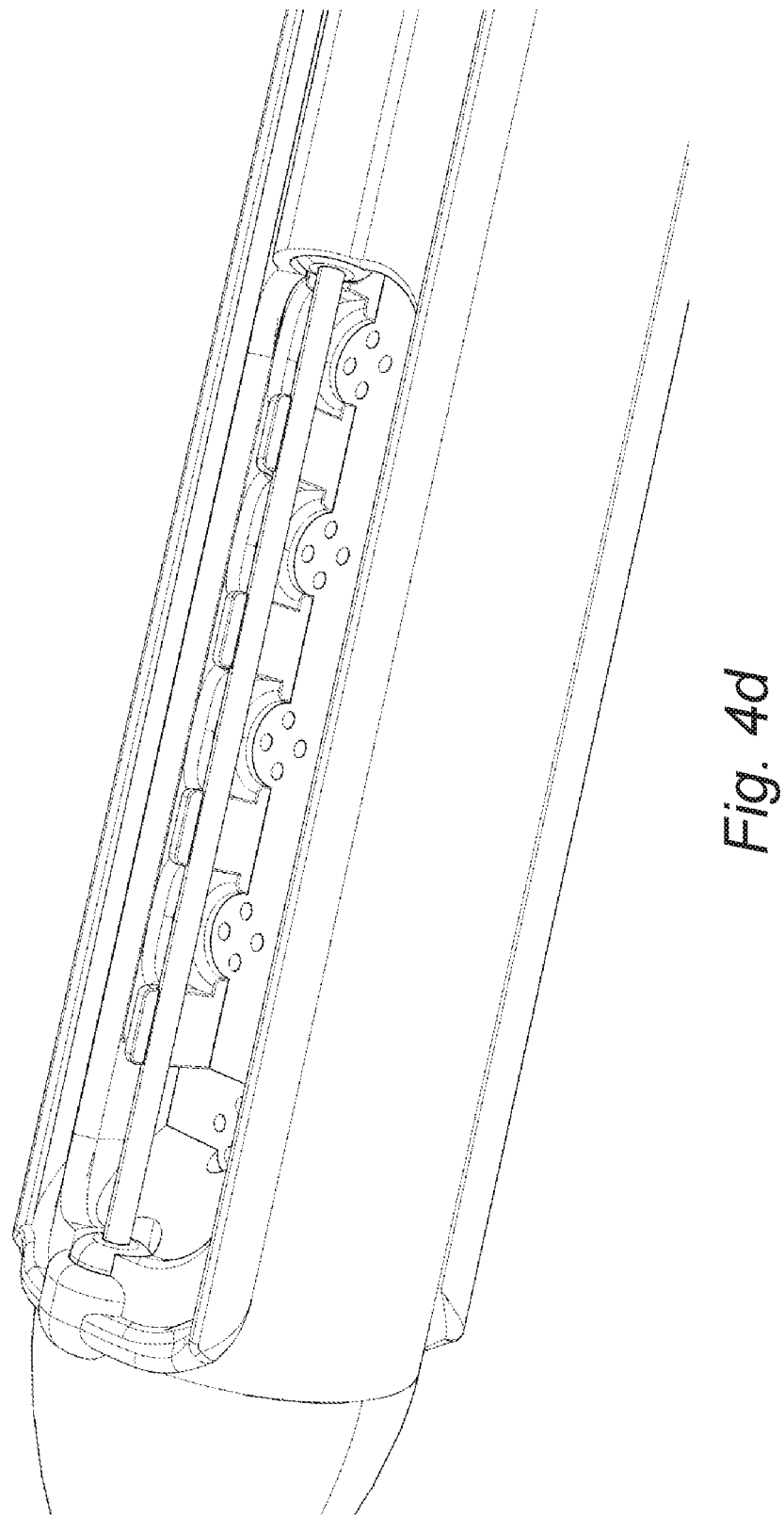
FIG. 4d illustrates selected parts of the device in FIG. 1 after the needle is inserted and with the first part of the mucosa support device removed.
Figure 4E:
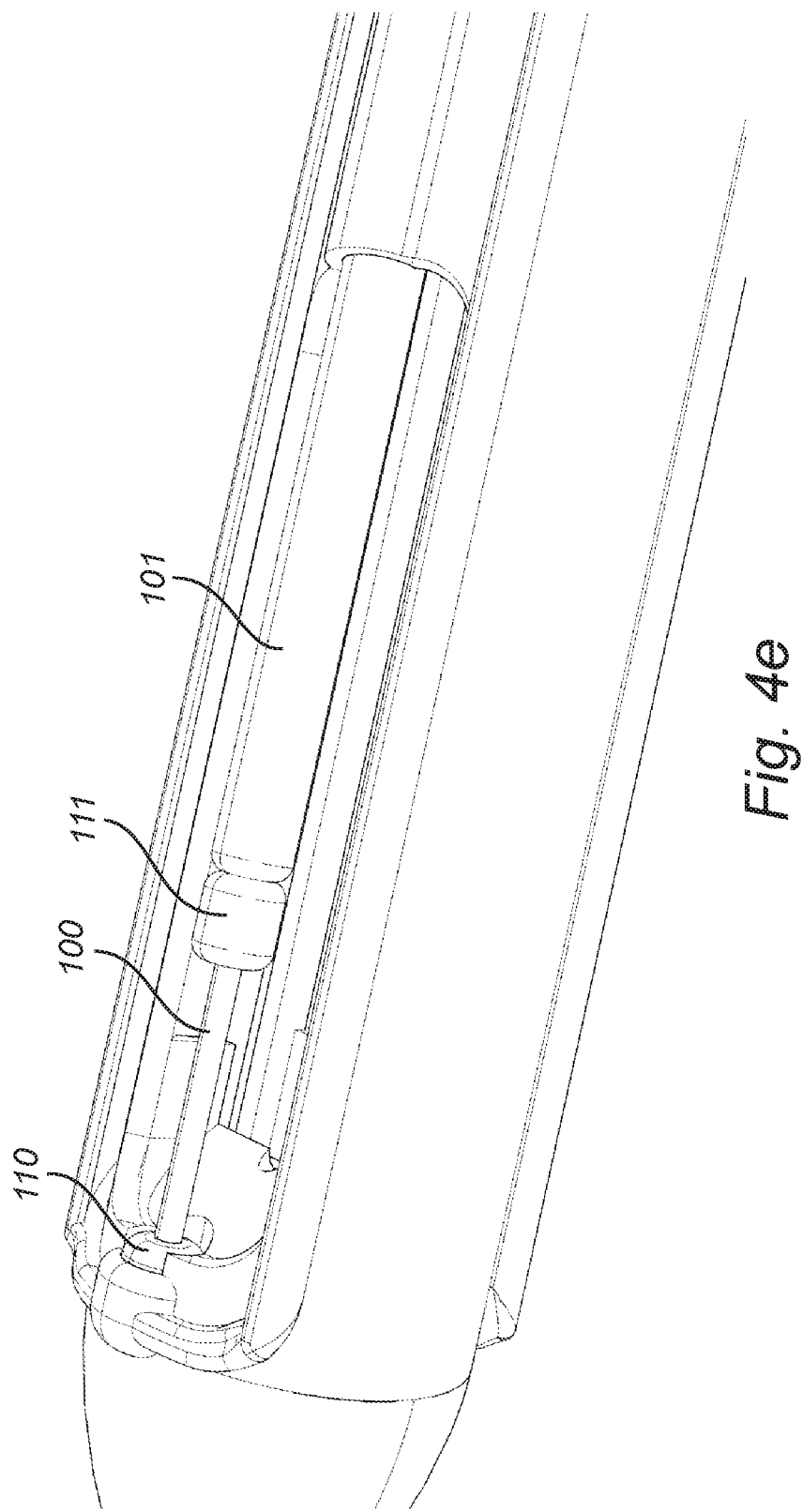
FIG. 4e illustrates selected parts of the device in FIG. 1 during tensioning of the fastening means.
Figure 5:
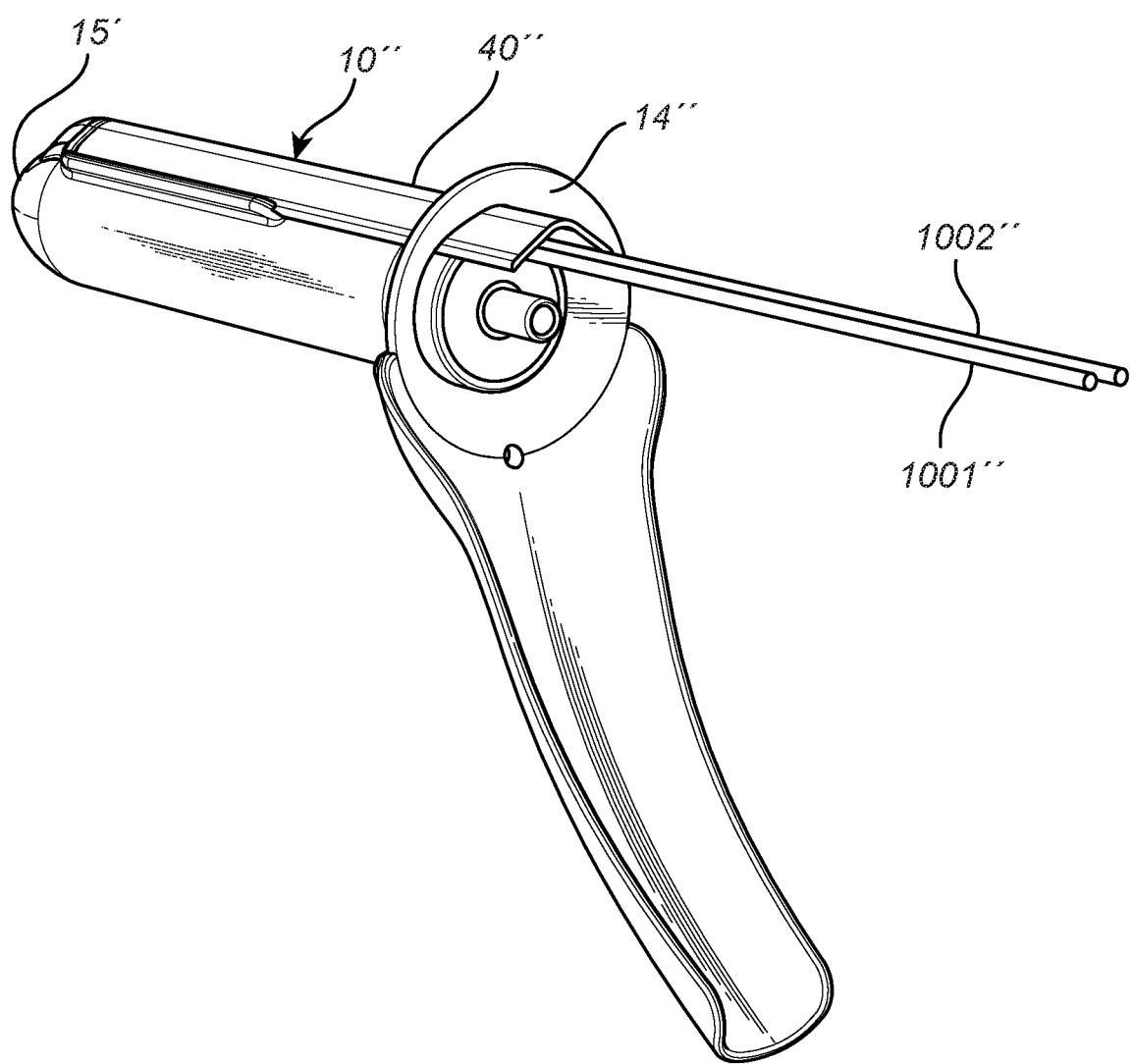
FIG. 5 illustrates a second embodiment of the device according to the invention in perspective.
Figure 6:
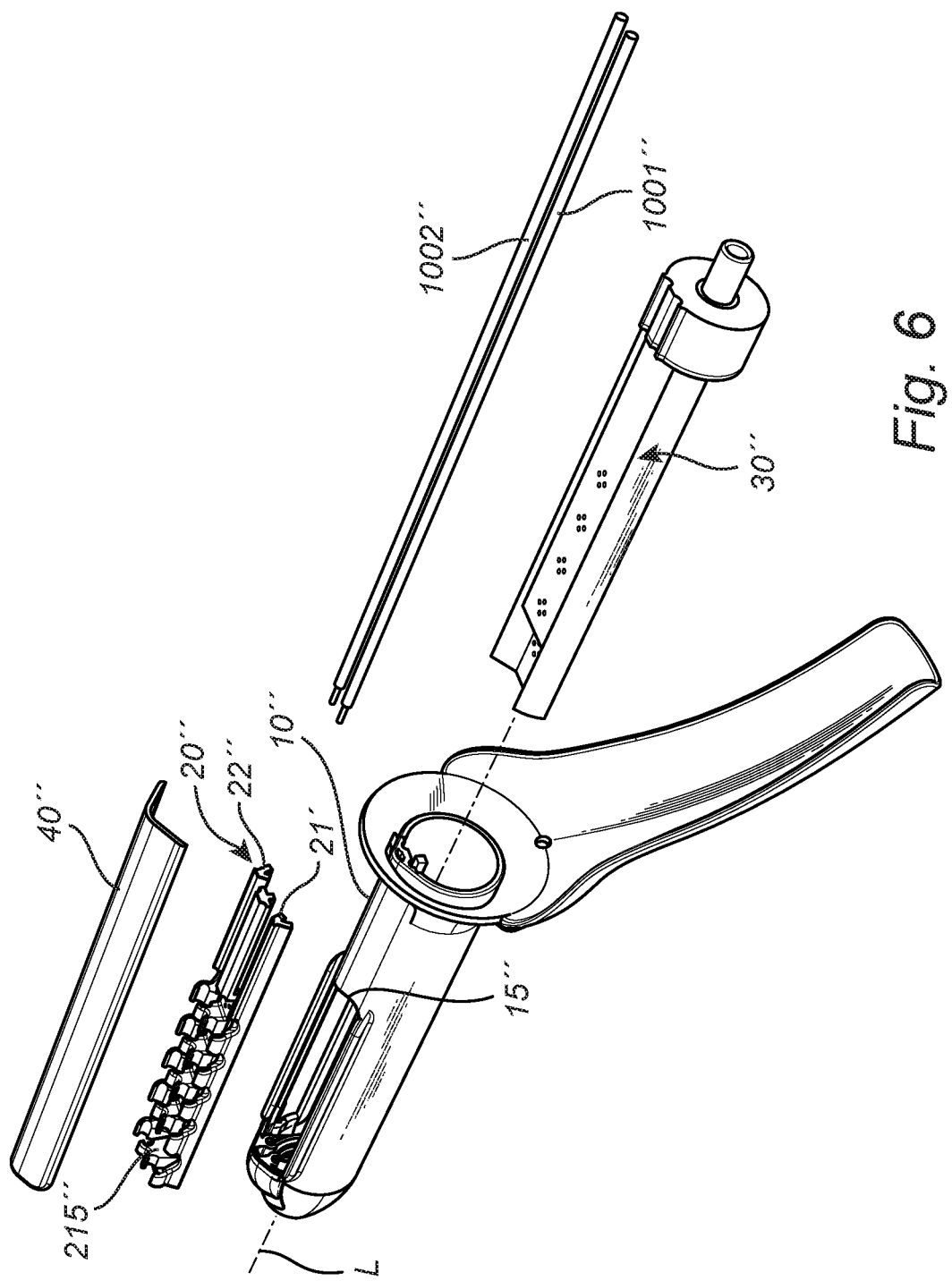
FIG. 6 illustrates an exploded view of the second embodiment of the device according to the invention in perspective.
Figure 7:
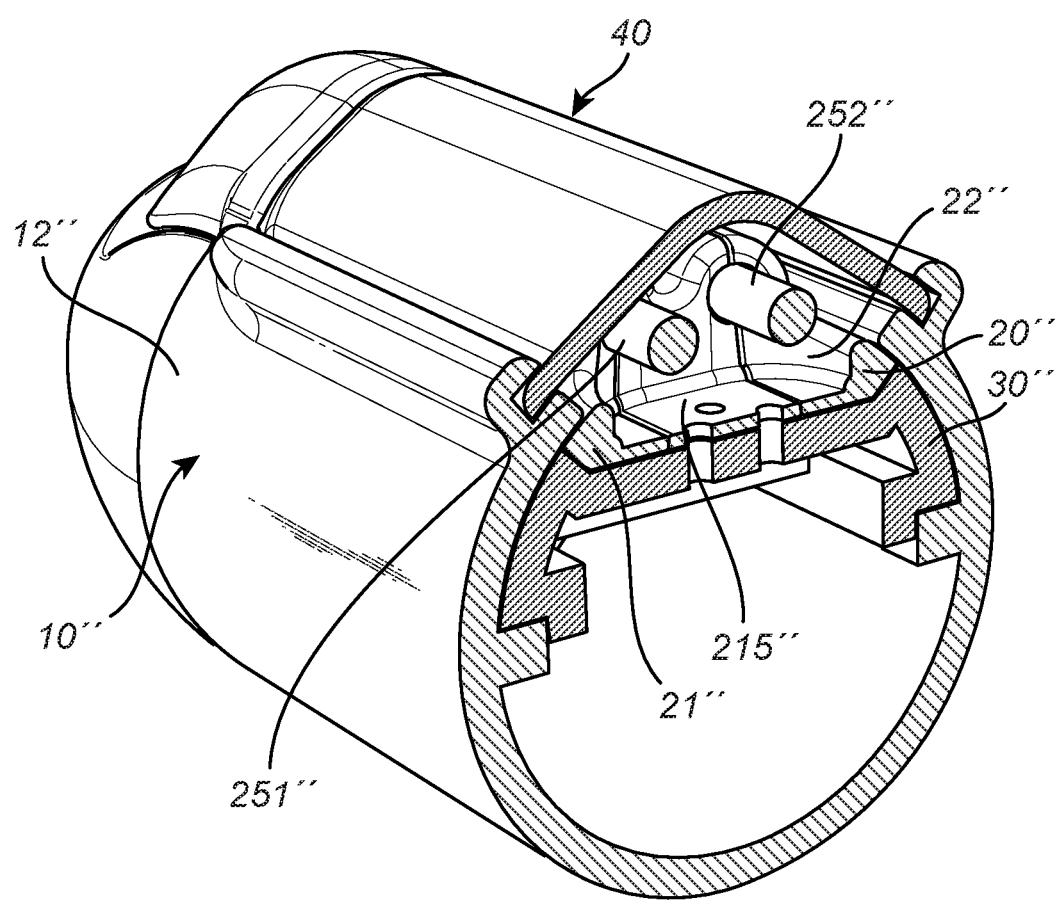
FIG. 7 illustrates a cross sectional view of the second embodiment of the device through a plane transverse to the longitudinal axis.
Figure 8:
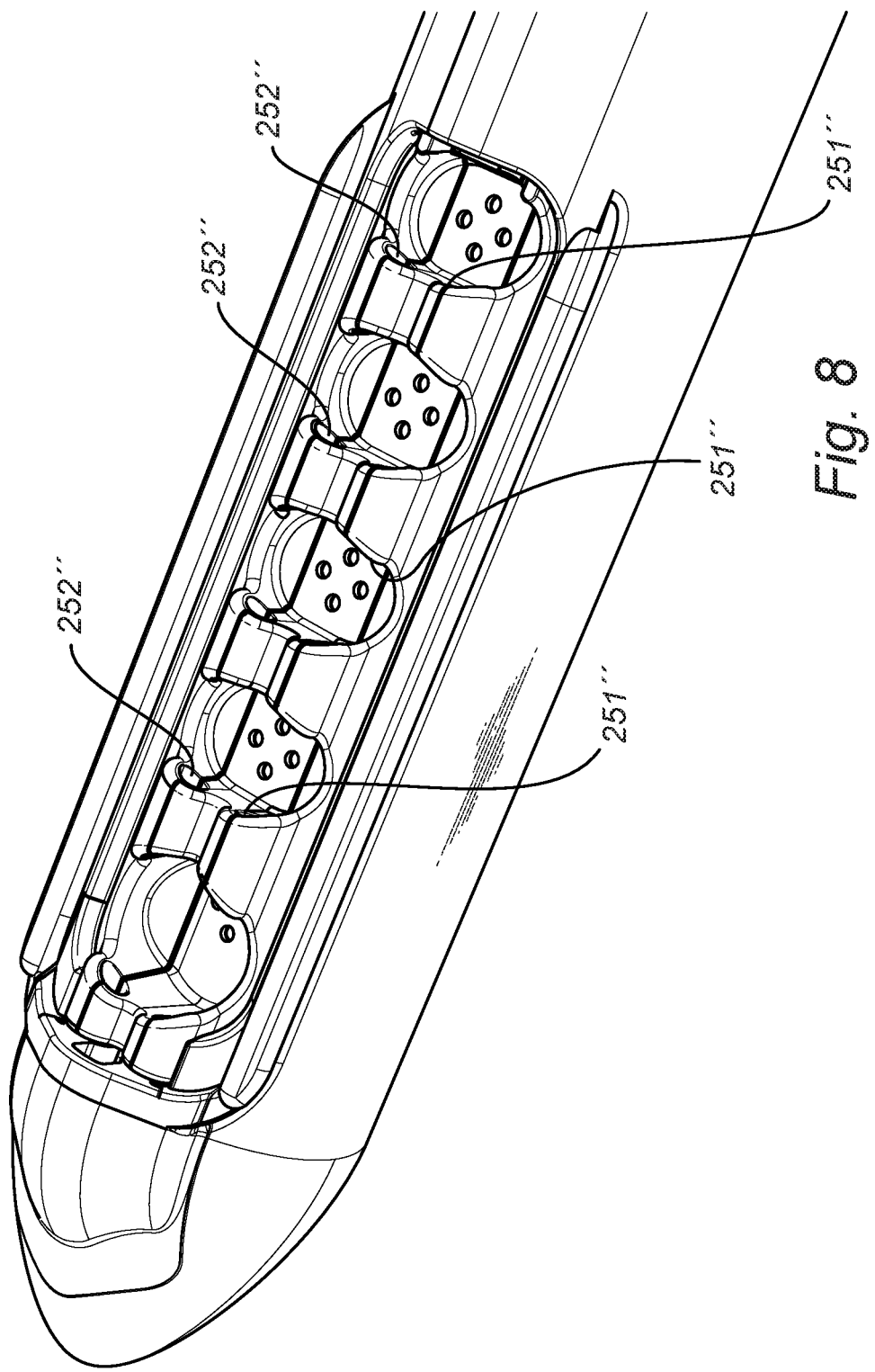
FIG. 8 illustrates selected parts of the second embodiment of the device.

In FIGS. 4b, 4c and 4d perspective views of the anal mucosa support device and a needle moved to the position where it is extending through the cavities are illustrated. In order to more clearly illustrate the anal mucosa support device and needle, the anal mucosa is not illustrated. In FIG. 4d one of the elongated parts 21 of the anal mucosa support has been removed to more clearly illustrate the needle and the needle passages 25 formed between the first and second elongated part. In FIG. 4e, both the first 21 and second 22 elongated part of the anal mucosa support and the locking element 30 are removed.

The claimed device for use in the treatment of hemorrhoids may comprise more than one opening in the tube-shaped element and corresponding anal mucosa support devices and needle guide structures to make it possible to perform surgical treatment in two or more regions within the rectum of the patient without changing the position of the device. The fact that treatment could be made in further areas reduces the overall time for the surgical treatment.

An alternative embodiment of the device according to the invention is illustrated in FIGS. 5, 6, 7 and 8. This embodiment comprises two needle guide structures formed in the elongated tube-shaped element and the anal mucosa support device such that two needles could be guided during movement within the tube-shaped element from an extracted position in which the needles are arranged outside the opening in the elongated tube-shaped element across the at least two cavities in the anal mucosa support device to a position where the needles extend across the opening in the tube-shaped element. This embodiment is favourable since this embodiment provides for two suture wires, stamps or other such securing arrangements side by side which provides an improved lifting effect when the suture thread, staple or other such securing means are tightened, and provides a stronger more resistant lifting effect.

This embodiment of the device 1O" comprises the same type of elongated tube-shaped element 12" with a rounded forward end 13", preferably removably connected to the body of the tube-shaped element to facilitate assembly of the different components of the device, and the slightly curved open aft 14". The length, cross-sectional shape and diameter could be adapted to suit different patients.

In the tube-shaped element, the same type of opening 15" is formed between the forward 13" and aft end 14". The opening 15" has a substantially constant width along the direction parallel to axis L.

The anal mucosa support device 20" comprises a first 21", a second 22" and an intermediate 215 elongated part arranged to extend substantially parallel to axis L.

The first and second part are arranged on opposite sides of the intermediate part adjacent to the intermediate part such that one needle passage 251" is formed in the contact surface between the first part and the intermediate part, and the second needle passage 252" is formed in the contact surface between the intermediate part and the second elongated part.

The anal mucosa support device 20" is removably arranged within the tube shape element such that the anal mucosa support device 20" is exposed in the opening 15". The anal mucosa support device comprises four cavities 23" with substantially equal size and a larger fifth cavity 24" formed in the forward end.

The first, second and intermediate part are designed to be arranged adjacent to each other and the first and second needle passages 251" and 252" are formed along the contact surface between the first and intermediate part, and the intermediate and second part. The illustrated embodiment of the device comprises five needle passages. The needle passages constitute the needle guide structure that provides the desired guide for the respective needle 1001", 1002" during movement within the tube-shaped element from the extracted position through the cavities.

The anal mucosa support device is removably arranged within the tube-shaped element and maintained in the intended position within the tube-shaped element by a removable locking element 30" as described above in relation to the first embodiment of the device. In the same way as above, a device according to the invention comprising an anal mucosa support device and one locking element has been described but the device could comprise two, alternatively three or more, corresponding substantially identical arrangements. If the device comprises two arrangements which are illustrated in FIG. 3, the openings are arranged opposite to each other in the tube-shaped element and if the device comprises three, or more, arrangements these are arranged at substantially equal distance from each other around the tube-shaped element.

Different types of suture wires, stamps or other such securing arrangements as understood by persons of ordinary skill in the art could be used in combination with the device according to the invention and when the needle and suture thread, staple or other such securing means is arranged extending through the anal mucosa, the needle is removed and the suture thread, staple or other such securing means is tightened and permanently secured such that the desired lift of the prolapsed anal mucosa is achieved.

In the appended drawings different embodiments of the device according to the invention are illustrated. A plurality of the components of the device may however be modified in a plurality of ways without departing from the scope of the invention as defined by the appended claims.

The device according to the invention could be used in combination with different alternatives to secure the anal mucosa in the lifted position and three possible options will now be described with reference to the corresponding figures.

Figure 9:
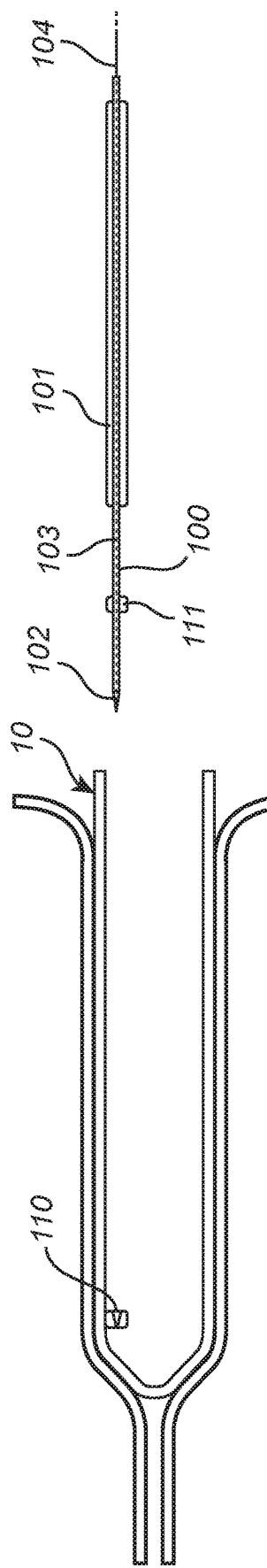
FIG. 9 illustrates schematically the use of suture thread for lifting the anal mucosa.

The first alternative is schematically illustrated in FIG. 9. In the forward end of the device 10, a forward stop element 110 is removably arranged forward of the opening 15 in the tube-shaped element 12 before the treatment is initiated. The needle comprises a needle tip 102 and a needle body 103 shaped like a tube. The needle tip is releasable from the needle body and a suture thread 104 with a length exceeding the needle body length is extending from the aft end of the needle body through the needle body to the needle tip 102 where it is permanently secured in the needle tip 102. The stop element 110 is positioned in the intended forward position of the needle tip 102. When the device 10 is in the desired position within the rectum of the patient, the needle is moved from the retracted position through the cavities to the forward stop element 110 where the needle tip 102 penetrates the forward stop element 110 and permanently secures to the forward stop element 110. The permanently securing between the forward stop element and the needle tip could be achieved in different ways. For example, a male/female fitting may be used. The needle body 103 is then retracted to free the suture thread 104 that is extending through the anal mucosa. Once the needle body is removed, also the sealing plug 50, the locking element 30 and the anal mucosa support device 20 are removed to free the thread and the anal mucosa from the anal mucosa support device. In order to achieve the desired lift of the anal mucosa an aft stop element 111 is pushed forwards along the thread to force the anal mucosa folds towards the forward stop element 110. The aft stop element 111 and the suture thread 104 are either provided with a corresponding securing structure that prevents the rear stop element 111 from moving backwards along the thread or permanently secured in the desired position by for example a knot. The aft stop element 111 is either arranged on the thread and positioned forward of the needle sleeve 101 before the treatment is initiated or arranged on the thread once the needle body and needle sleeve are removed from the thread.

Figure 10:
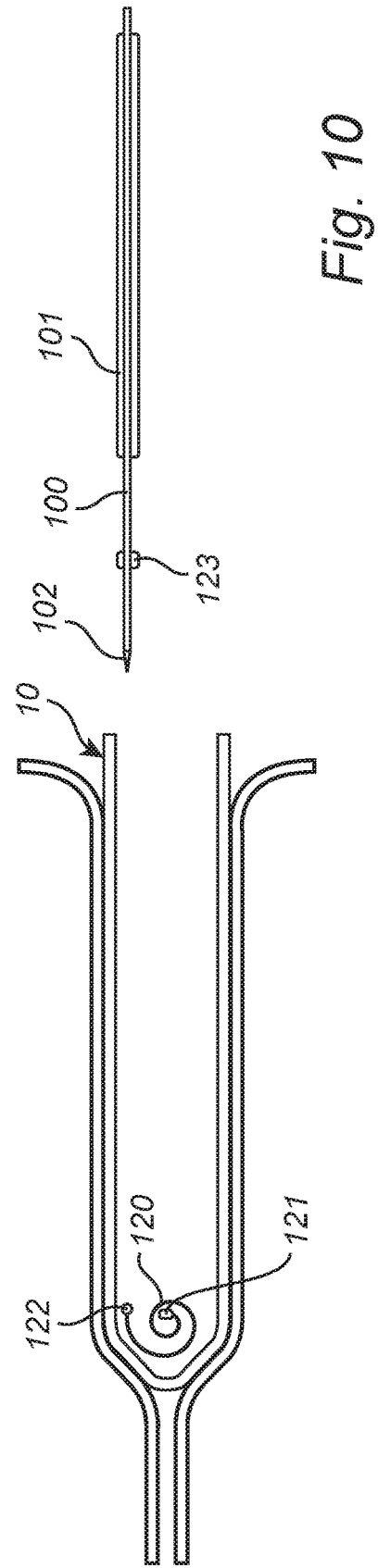
FIG. 10 illustrates schematically a second embodiment of use of suture thread for lifting the anal mucosa.

A second alternative is illustrated in FIG. 10. Within the forward end of the device 10, a suture thread 120 is arranged inside the device before the treatment is initiated. In one end of the suture thread a forward stop element 121 is permanently secured and in the opposite end of the suture thread docking means 122, for example a loop or male/female fitting, are arranged. The docking means 122 are positioned in the intended forward position of the needle tip 102. When the device 10 is in the desired position within the rectum of the patient, the needle 100 is moved from the retracted position through the cavities to the docking means 122 where the needle tip 102 connects to the docking means 122 such that the needle is connected to the docking means 122. The needle is then retracted together with the suture thread to a position where the forward stop element 120 rest against the forward fold of the anal mucosa. Once the needle is removed, also the sealing plug 50, the locking element 30 and the anal mucosa support device 20 are removed to free the thread 120 and the anal mucosa from the anal mucosa support device. In order to achieve the desired lift of the anal mucosa an aft stop element 123 is pushed forwards along the thread to force the anal mucosa folds towards the forward stop element 121. The aft stop element 123 and the suture thread 120 are either provided with a corresponding securing structure that prevents the rear stop element 123 from moving backwards along the thread or permanently secured in the desired position by for example a knot. The aft stop element 123 is arranged on the thread once the needle and needle sleeve are removed from the thread.

A very simple and reliable embodiment based on this general idea involves an elongated suture thread arranged loaded within the device before the surgery is initiated. One end of the suture thread comprises a docking element 122. Once the needle is introduced the needle tip is connected to the docking element 122 and the thread introduced through the anal mucosa when the needle is retracted. The length of the suture thread is at least long enough to ensure that the both ends of the suture thread extend all the way out through the open end of the device such that the surgeon can secure the ends of the thread by one or more knots and lift the anal mucosa.

This embodiment is also very favorable in combination with the embodiment of the device comprising two parallel needles since one single suture thread could be arranged in the forward end of the device with one end provided with docking means 122 positioned in the forward end of one needle, and the second end of the suture thread provided with similar docking means 122 positioned in the forward end of the other needle. Once the two needles have docked to the corresponding docking mean 122 both ends of the suture thread are retracted through the folds of the anal mucosa such that both ends are extending out of the aft end of the device. After the desired lift of the anal mucosa is achieved the two ends could be secured by one, or more, reliable knots.

A third alternative is illustrated in FIG. 11. In the forward end of the device 10, a forward stop element 130 is removably arranged forward of the opening 15 in the tube-shaped element 12 before the treatment is initiated. From the forward stop element 130 a suture thread 131 is extending to the aft end of the tube-shaped element 12. The needle comprises a needle tip 102 and a needle body 103 shaped like a pipe. The needle tip is releasable from the needle body and a suture thread 132 with a length exceeding the needle body length is extending from the aft end of the needle body through the needle body to the needle tip 102 where it is permanently secured in the needle tip 102. The stop element 130 is positioned in the intended forward position of the needle tip 102. When the device 10 is in the desired position within the rectum of the patient, the needle is moved from the retracted position through the cavities to the forward stop element 130 where the needle tip 102 penetrates the forward stop element 130 and permanently secures to the forward stop element 130. The permanently securing between the forward stop element and the needle tip could be achieved in different ways like for example a male/female fitting. The needle body 103 is then retracted to free the suture thread 132 that is extending through the anal mucosa. Once the needle body is removed, also the sealing plug 50, the locking element 30 and the anal mucosa support device 20 are removed to free the thread 132 and the anal mucosa from the anal mucosa support device. The anal mucosa arranged along the suture thread 132 is pushed forwards along the thread to force the anal mucosa folds towards the forward stop element 130. The suture thread 132 extending from the needle tip 102 and the suture thread 131 extending from the forward stop element 130 are then secured together by one or more knots to secure the anal mucosa in the lifted position.

A fourth possible alternative is a combination of the previously described alternatives. This alternative is not illustrated in any figure. Within the forward end of the device 10, a suture thread is arranged before the treatment is initiated. Close to the center of the suture thread a forward stop element is permanently secured on the suture thread. One of the ends of the suture thread is lead to a position outside the aft end of the device. The other end of the suture thread is ended by docking mean, for example a loop or male/female fitting, arranged in the position of the needle tip in the forward position. When the device is in the desired position within the rectum of the patient, the needle is moved from the retracted position through the cavities to the docking means where the needle tip connects to the docking means. The needle is then retracted together with the suture thread to a position where the forward stop element rest against the forward fold of the anal mucosa. Once the needle is removed, also the sealing plug, the locking element and the anal mucosa support device are removed to free the thread and the anal mucosa from the anal mucosa support device. The anal mucosa arranged along the suture thread is pushed forwards along the thread to force the anal mucosa folds towards the forward stop element. The two parts of the suture thread extending from the forward stop element then secured together by one or more knots to secure the anal mucosa in the lifted position.

A fifth embodiment, not illustrated, comprises a forward stop element arranged forward of the opening in the tube-shaped element. The needle comprises a needle tip and a needle body shaped like a tube. Once the needle has been introduced all the way to the forward end of the tube-shaped element, a suture thread is pushed forward via the needle body towards a guiding surface within the forward end of the tube-shaped element such that the direction of the suture thread is changed and the forward end of the suture thread is moved backwards towards the open aft end of the tube-shaped element when the suture thread is pushed further into the tube-shaped element. Once the desired lift of the anal mucosa is achieved the forward and aft end of the suture thread are secured together by for example a knot.

The invention claimed is:
1. A device for use in the treatment of hemorrhoids, said device comprising:
  an elongated tube-shaped element comprising a forward end and an aft end, said aft end providing access to the interior of the tube-shaped element, said tube-shaped element extending along a longitudinal axis L and comprising at least one opening formed between the forward and aft end; and an anal mucosa support device removably arranged within the tube shape element, said support device comprising at least two cavities to receive anal mucosa; and a sealing plug arranged to close and seal the open aft end of the device and a connection with access to the interior of the tube-shaped element, said connection is intended to be connected to pumping means such that the pressure within the tube-shaped element could be reduced and the anal mucosa sucked into the at least two cavities, wherein at least one needle guide structure is formed in the elongated tube-shaped element and the anal mucosa support device such that at least one needle is capable of being guided during movement within the tube-shaped element across the at least two cavities in the anal mucosa support device to a position where the needle extends across the opening in the tube-shaped element.

2. The device according to claim 1, wherein the at least one needle is moved from an extracted position outside the tube-shaped element to a position where the needle extends across the opening in the tube-shaped element parallel to its longitudinal axis L.

3. The device according to claim 1, wherein the at least one needle guide structure comprises at least one needle passage arranged in the opening in the elongated tube-shaped element to guide the at least one needle during movement from the extracted position to the position where the needle extend across the opening in the tube-shaped element.

4. The device according to claim 3, wherein the at least one needle passage is formed in a contact surface between the elongated tube-shaped element and the anal mucosa support device such that the at least one needle passage is opened when the anal mucosa support device is removed from the elongated tube-shaped element.

5. The device according to claim 3, wherein the anal mucosa support device comprises at least a first and a second elongated part extending substantially parallel to axis L, said first and second part are arranged adjacent to each other and the at least one needle passage formed in a contact surface between the first and second elongated part such that the at least one needle passage is opened when the first and second elongated part are separated from each other.

6. The device according to claim 3, comprising two needle guide structures formed in the elongated tube-shaped element and the anal mucosa support device such that two needles are guided during movement within the tube-shaped element from an extracted position in which the needles are arranged outside the opening in the elongated tube-shaped element across the at least two cavities in the anal mucosa support device to a position where the needles extend across the opening in the tube-shaped element.

7. The device according to claim 6, characterized in that the anal mucosa support device comprises a first, a second and an intermediate elongated part extending substantially parallel to axis L, said first and second part are arranged on opposite sides of the intermediate part adjacent to the intermediate part such that a first needle passage is formed in the contact surface between the first part and the intermediate part, and a second needle passage is formed in the contact surface between the intermediate part and the second elongated part such that the two needle passages are opened when the first, second and intermediate elongated part are separated from each other.

8. The device according to claim 6, wherein the two needle guide structures are arranged to guide the two needles substantially parallel from the extracted position in which the needles are arranged outside the opening in the elongated tube-shaped element across the at least two cavities in the anal mucosa support device to the position where the needles extend across the opening in the tube-shaped element.

9. The device according to claim 1, wherein the at least one needle guide structure comprises at least one needle guide element arranged in the elongated tube-shaped element on either side of the opening in the tube-shaped element to guide the needle.

10. The device according to claim 1, wherein the tube-shaped element is divided into at least a forward and a rear part and said forward part is removably attached to the rear part.

11. The device according to claim 1, the sealing plug comprises the connection intended to be connected to pumping means.

12. The device according to claim 1, wherein the device comprises a handle extending in substantially radial direction from the longitudinal axis L from the aft end of the tube-shaped element and the connection with access to the interior of the tube-shaped element is arranged in the handle.

13. The device according to claim 1, wherein the at least two cavities in the anal mucosa support device comprises a bottom structure and the distance in radial direction from axis L between the centre of the needle passage and the bottom structure is between 2 and 12 mm.

14. The device according to claim 13, wherein the bottom structure comprises at least one opening in each cavity such that the anal mucosa is sucked into the at least two cavities.

15. The device according to claim 1, wherein the at least two cavities in the anal mucosa support device comprises a bottom structure, and the cavity arranged in the forward end of the anal mucosa support device along axis L have a larger distance in radial direction from axis L between the centre of the needle passage and the bottom structure than the at least one other cavity.

16. The device according to claim 1, wherein the anal mucosa support device is maintained in the intended position within the tube-shaped element by a removable locking element arranged within the tube-shaped element to force the anal mucosa support device into the intended position with the two cavities exposed in the opening of the tube-shaped element.

17. The device according to claim 16, wherein the locking element is forming a bottom structure in the cavities in the anal mucosa support device.

18. The device according to claim 16, wherein the closing element has a shape corresponding to the shape of the tube-shaped element.

19. The device according to claim 1, further comprising at least one closing element removably arranged in the tube-shaped element to close the at least one opening in the tube-shaped element and facilitate insertion of the device.

* * * * *